United States Patent

Williams et al.

[11] Patent Number: 5,811,662
[45] Date of Patent: Sep. 22, 1998

[54] RESISTIVE GAS SENSING, ESPECIALLY FOR DETECTION OF OZONE

[75] Inventors: David Edward Williams, Abingdon, United Kingdom; Patrick Timothy Moseley, Chapel Hill, N.C.; Peter McGeehin, Compton, United Kingdom

[73] Assignee: Capteur Sensors & Analysers, Ltd., Didcot, United Kingdom

[21] Appl. No.: 765,657
[22] PCT Filed: Jun. 20, 1995
[86] PCT No.: PCT/GB95/01452
  § 371 Date: Aug. 25, 1997
  § 102(e) Date: Aug. 25, 1997
[87] PCT Pub. No.: WO95/35495
  PCT Pub. Date: Dec. 28, 1995

[30] Foreign Application Priority Data

Jan. 25, 1995 [GB] United Kingdom .................... 9501461

[51] Int. Cl.⁶ .............................. G01N 27/04; B05D 1/40; H01C 7/00
[52] U.S. Cl. .......................... 73/31.06; 73/23.2; 73/31.02; 422/90; 422/94
[58] Field of Search .................. 73/31.06, 23.2, 73/23.31, 31.02, 31.03

[56] References Cited

U.S. PATENT DOCUMENTS

| | | | |
|---|---|---|---|
| 4,581,204 | 4/1986 | Voit | 422/90 |
| 4,661,234 | 4/1987 | Takahashi et al. | 204/406 |
| 4,991,424 | 2/1991 | Lehto | 73/31.06 |
| 5,136,274 | 8/1992 | Shimomura et al. | 338/35 |
| 5,334,350 | 8/1994 | Friese et al. | 422/98 |
| 5,447,054 | 9/1995 | Modica et al. | 73/31.06 |
| 5,448,906 | 9/1995 | Cheung | 73/31.06 |
| 5,517,182 | 5/1996 | Yasunaga | 340/634 |
| 5,605,612 | 2/1997 | Park et al. | 204/429 |
| 5,621,162 | 4/1997 | Yun et al. | 73/23.34 |
| 5,633,081 | 5/1997 | Clough et al. | 428/331 |

*Primary Examiner*—Hezron E. Williams
*Assistant Examiner*—J. David Wiggins
*Attorney, Agent, or Firm*—James B. Middleton

[57] ABSTRACT

A resistive gas sensor having a $WO_3$ sensing element is especially useful for detection of low concentrations (1 ppm or less) of ozone in air. The $WO_3$ element is a porous layer with a 30–60% porosity and less than 50 micrometer thick, having in general a sufficiently open porous microstructure and high surface area to give satisfactory response to ozone. The sensor is used for detection of low ozone concentrations at a working temperature in the range from ambient to 600° C.

18 Claims, 7 Drawing Sheets

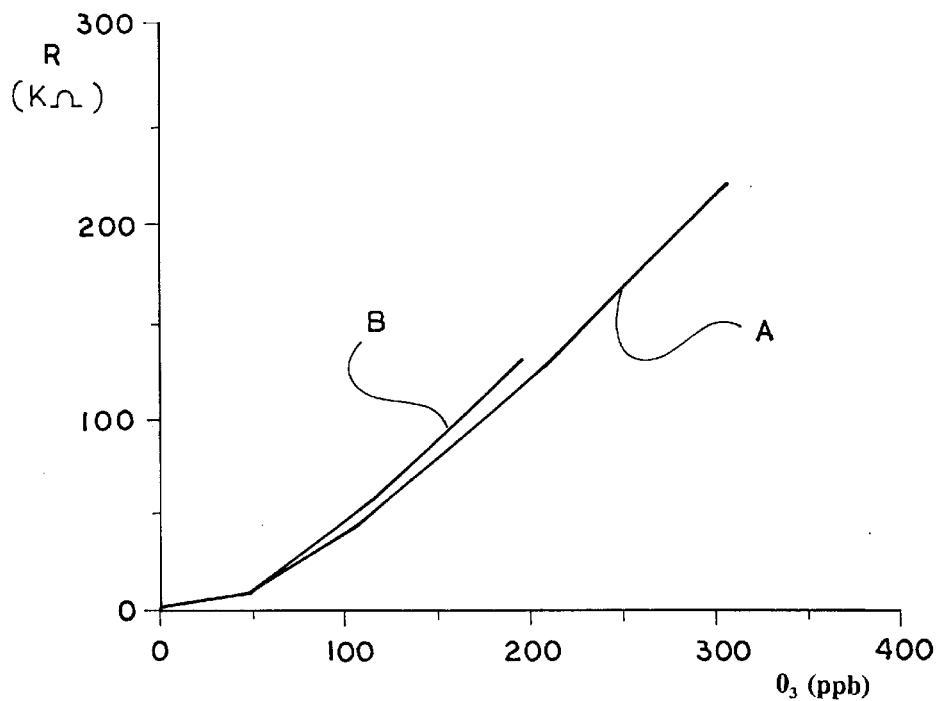
Fig_1
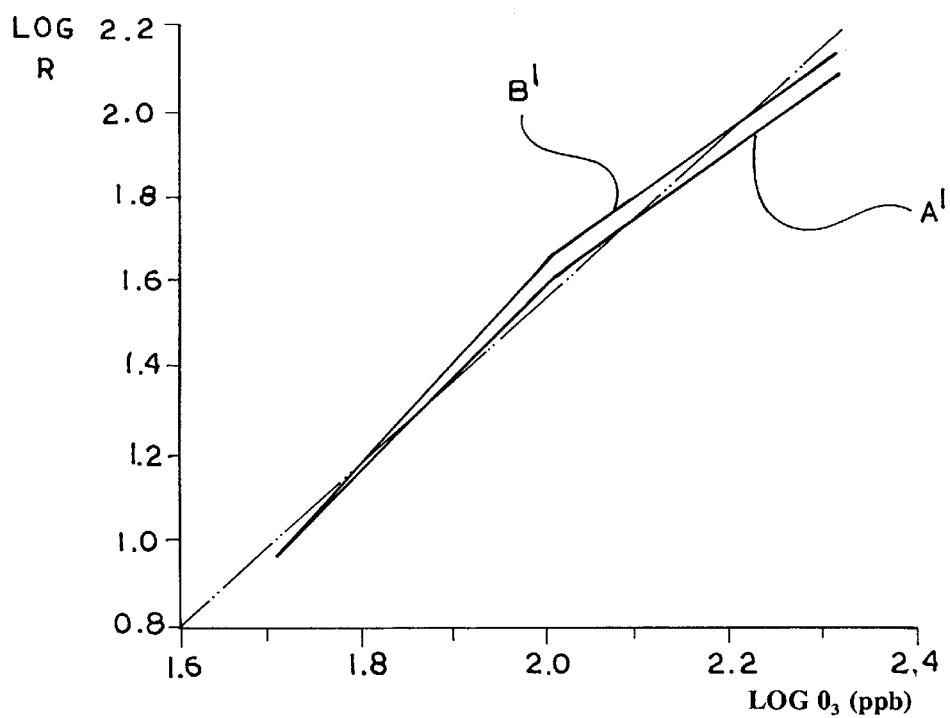
Fig_2

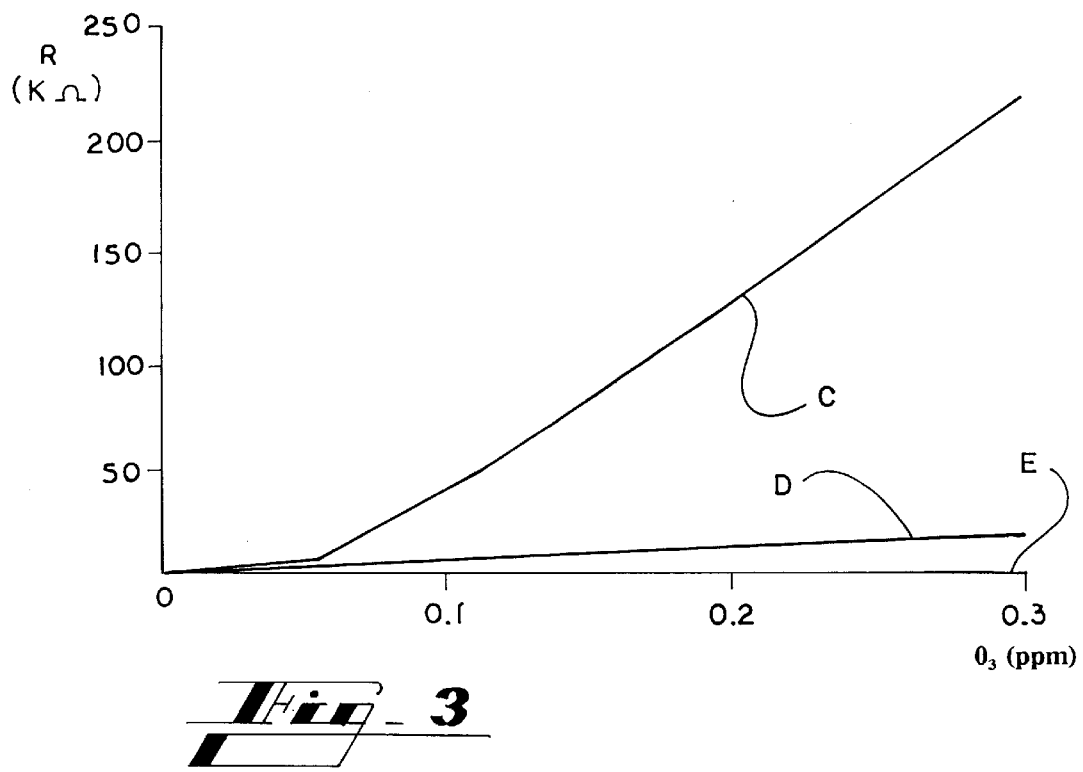
Fig. 3
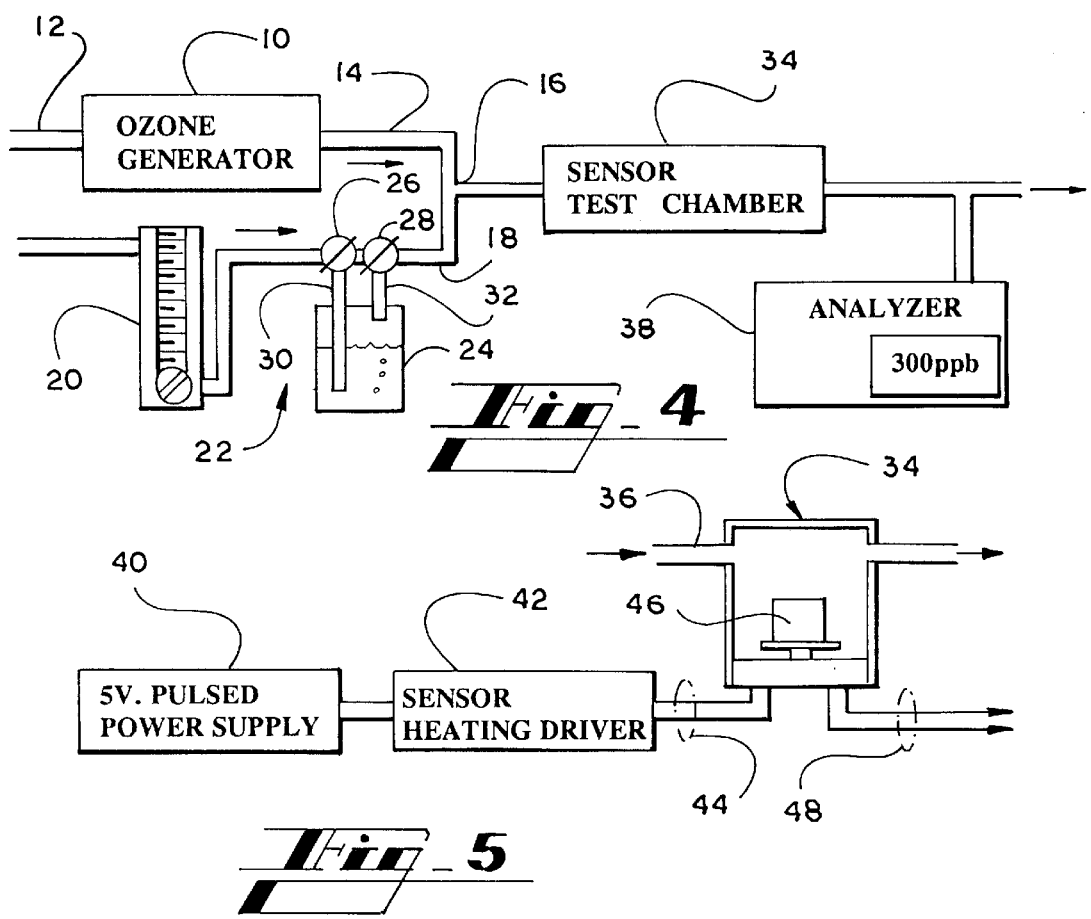
Fig. 4
Fig. 5

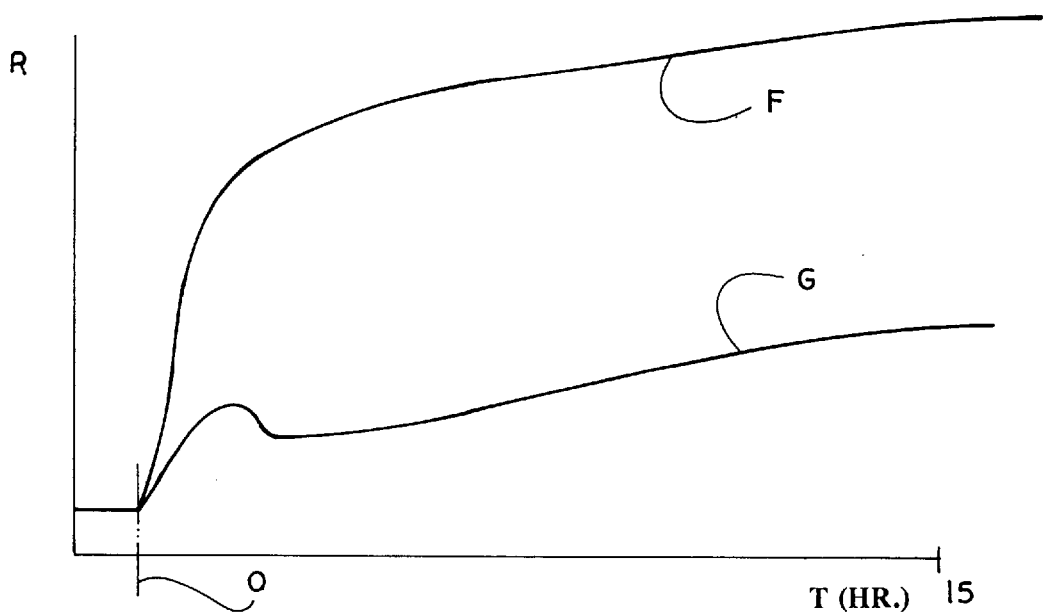
Fig_6
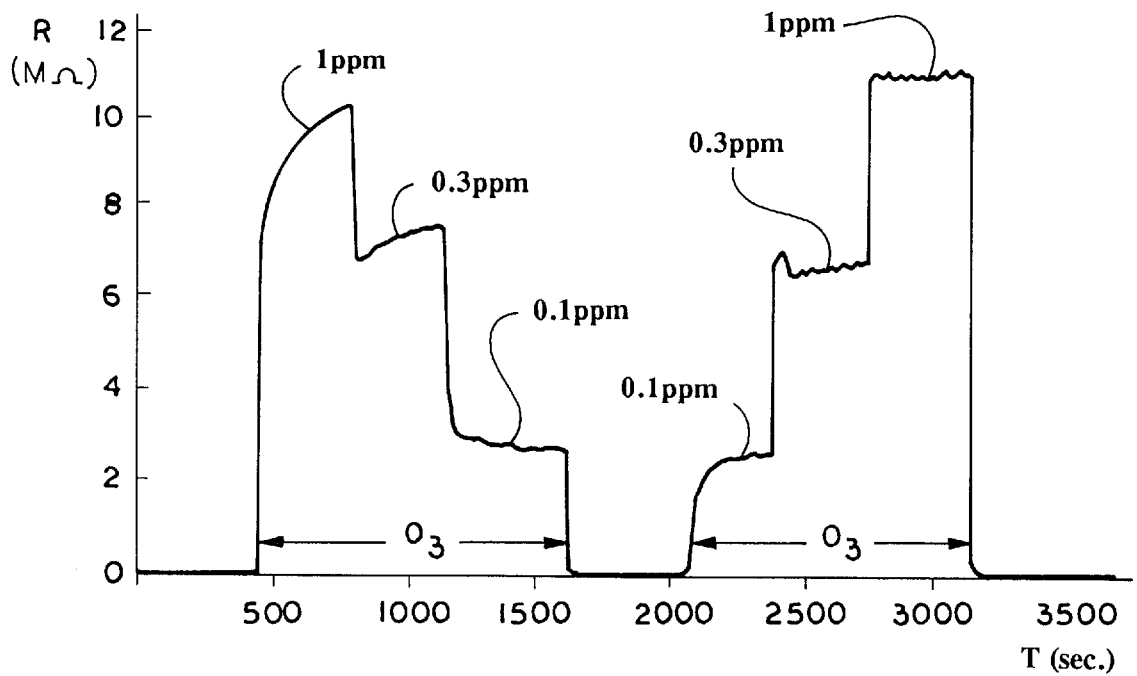
Fig_7

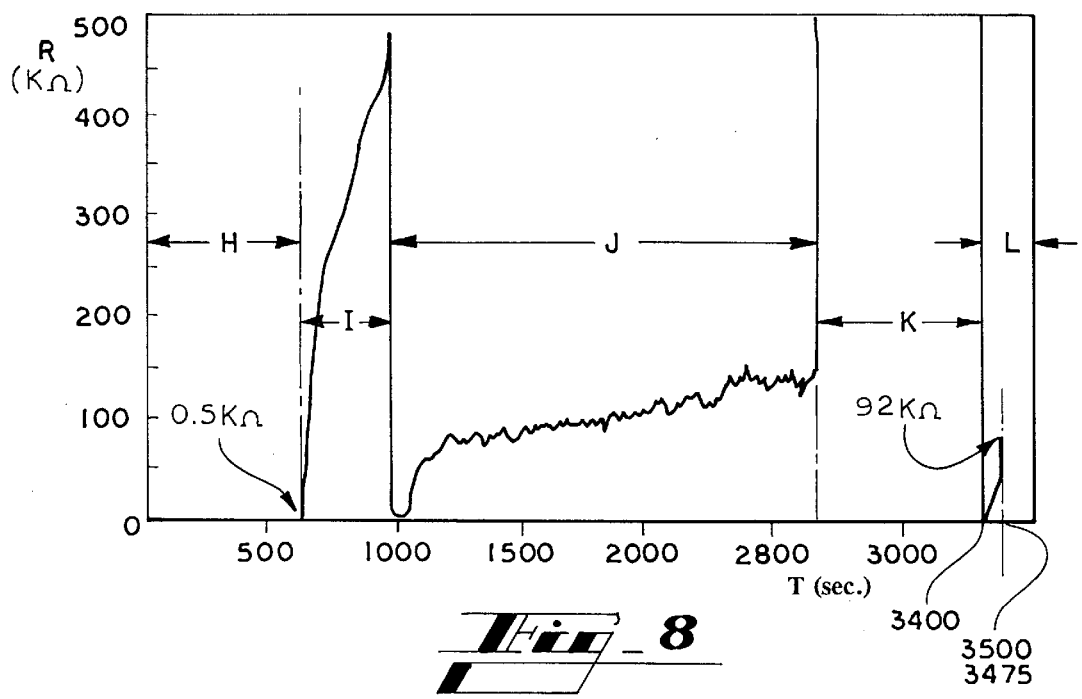
Fig_8
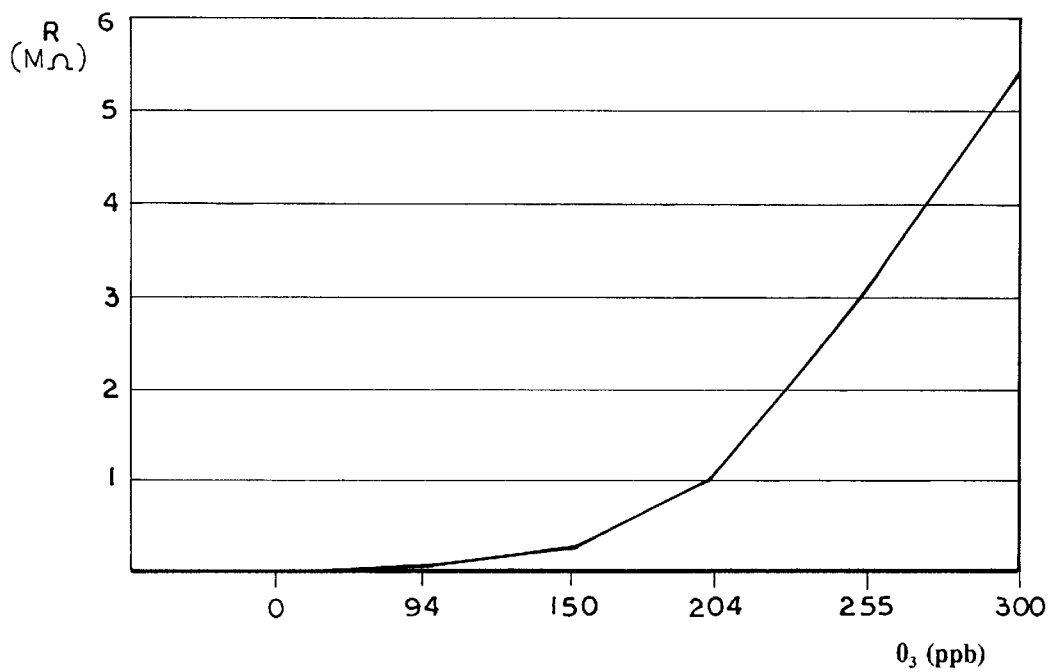
Fig_9

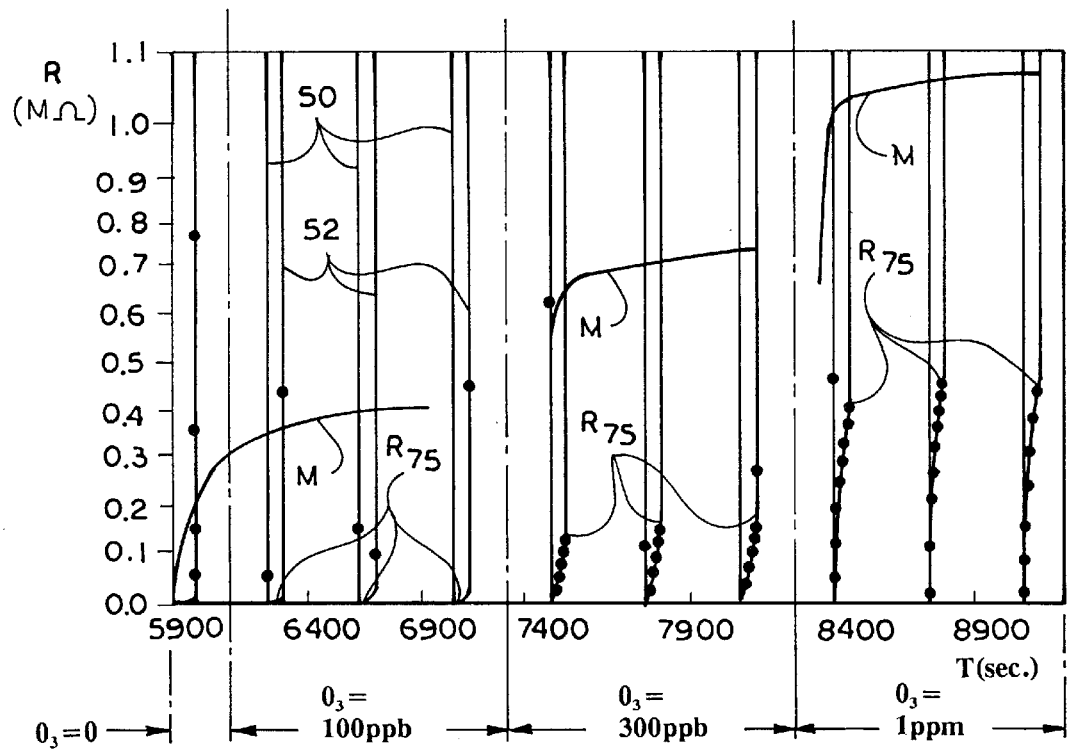
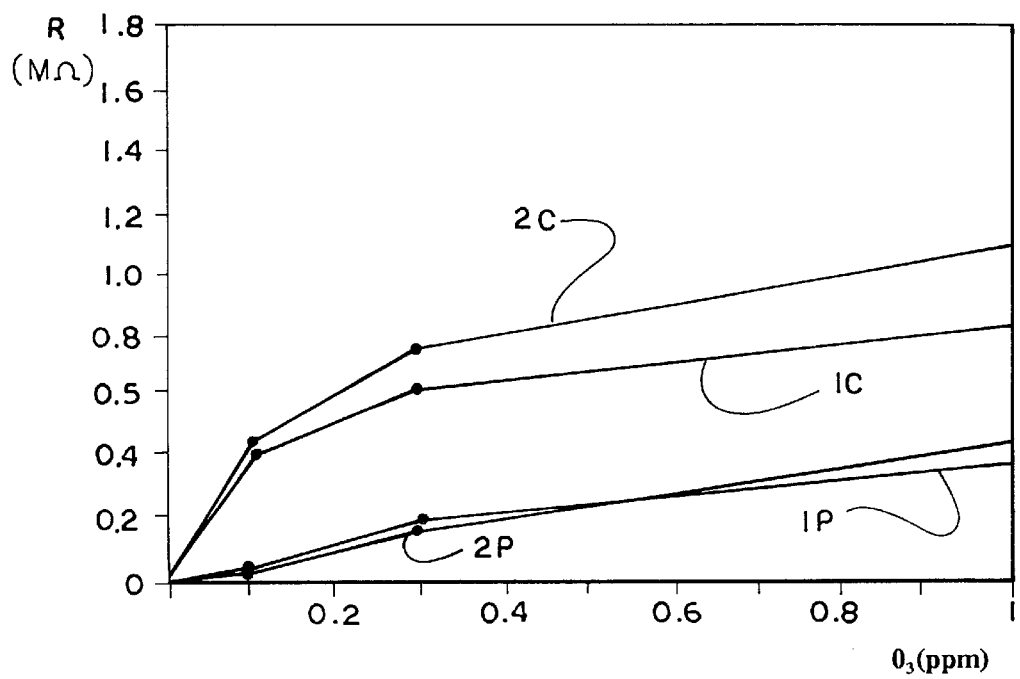

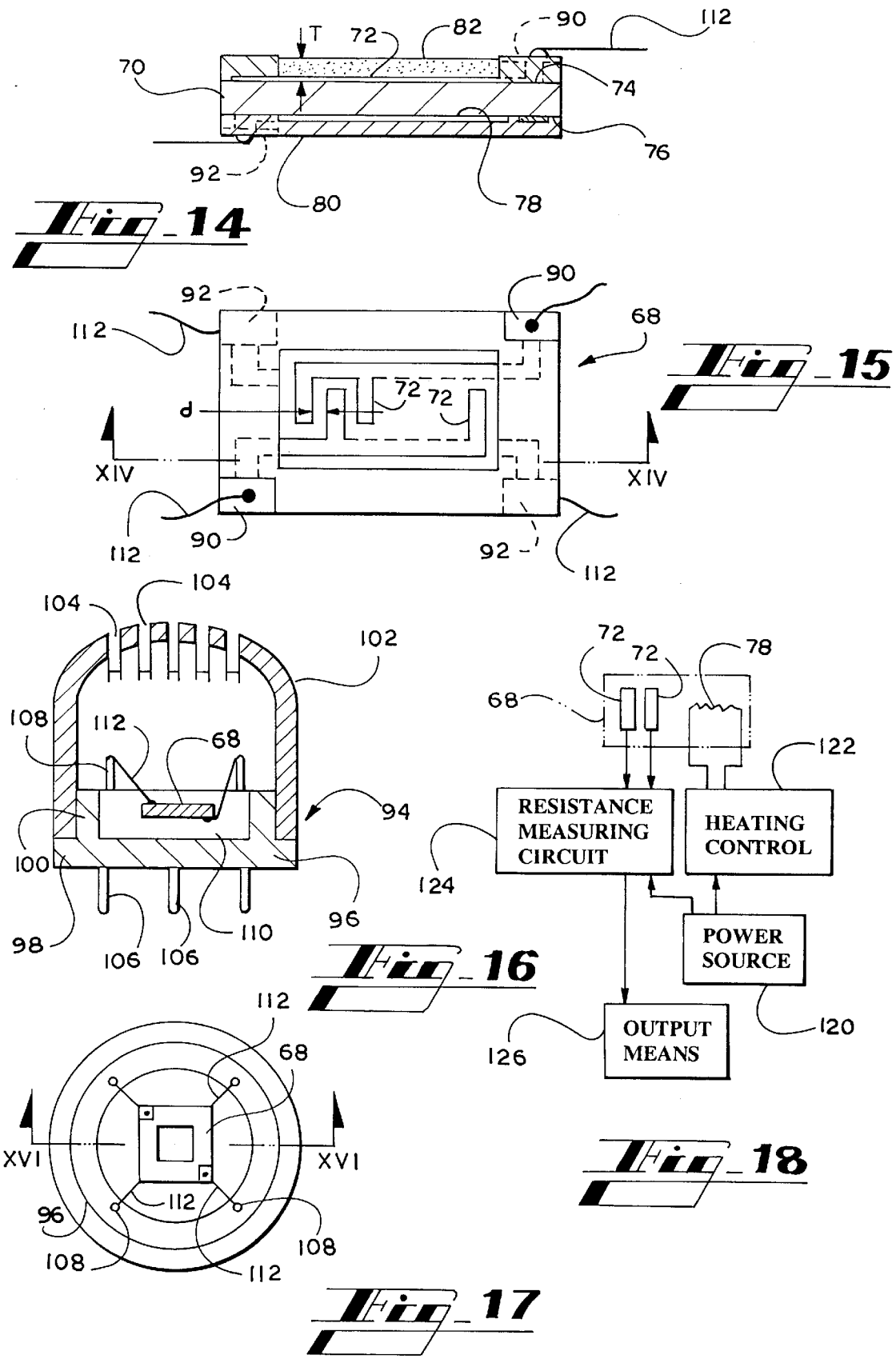

RESISTIVE GAS SENSING, ESPECIALLY FOR DETECTION OF OZONE

This invention relates to resistive gas sensing, especially for the detection of ozone, and in particular to methods of sensing ozone, sensors and sensing apparatus suitable for use in the measurement of ozone concentrations, and methods of making such sensors.

Our co-pending United Kingdom patent application GB 95 08115.4, filed on 21 Apr. 1995 with a priority date of 21 Apr. 1994, and not published at the date of the present application, discloses the use of tungsten trioxide ($WO_3$) as a material for gas sensors when incorporated in a fail-safe gas detection system in which the electrical resistance of the sensors increases with an increase in the concentration of a target gas consisting of chlorine, $NO_2$ or ozone.

The document WO95/00836, in the name of the present Applicants, discloses the use of $WO_3$ as the sensing material in gas sensors for the selective sensing of chlorine or $NO_2$ at a concentration of the order of 0.5 ppm (parts per million) in air, in such a way as to distinguish over the presence of any $SO_2$ or CO, the sensor having a heated thin-film sensing element which is preferably in the range of 10 to 200 micrometers thick.

It is well known to use sensors made from tungsten trioxide for the detection of hydrogen sulphide.

The document DE-A-3 213 286 (Hitachi) discloses a sensor in which the sensing material is $WO_3$ doped with platinum, for use in the detection, at a temperature in the range 250° to 400° C., of hydrogen, $NO_2$ or CO. The disclosure in the Hitachi document shows that this sensor gives a measurable signal only at concentrations of these gases in excess of about 1000 ppm, the doped $WO_3$ sensor being one of an array of sensors, of different materials, which are scanned in a particular way so as to give signals from the individual sensors.

Ozone in air can be toxic at concentrations of less than 1 ppm or 1000 ppb ("ppb" means parts per billion, where 1 billion is 1000 million). In the United Kingdom, occupational limits for exposure to ozone lie in the range 100–300 ppb.

One object of this invention is to provide gas sensors which are sensitive to ozone at these rarefied concentrations, in order for example to provide continuous monitoring of an atmosphere, giving electrical output signals which can be used to trigger warning devices and/or means for remedying hazardous occupational exposure levels of this gas.

In these circumstances, it is of course desirable to distinguish the presence of ozone from that of other gases which may be present at similar concentrations but which are harmless at these levels.

It is therefore another object of the invention to provide a sensor capable of detecting ozone at concentrations of less than 1 ppm in air in the presence of other gases, for example $H_2S$, CO, hydrocarbons, ammonia, hydrogen, ethanol, chlorine, or $NO_2$.

We have been surprised to find that these requirements can be satisfied by using $WO_3$ as the sensitive material in a sensor in a form having a very open porous microstructure with an especially large surface area exposed to the target gas.

According to the invention in a first aspect, a resistive gas sensor comprising a sensing element containing tungsten trioxide as gas-sensitive material, is characterised in that the sensing element is a porous oxide layer in which the oxide is at least 99% pure, its porosity being in the inclusive range 30–60%, macroscopic flaws having a dimension larger than 5 times the mean pore size being absent, and the layer having a thickness of less than 50 micrometer and uniform to an accuracy better than ±20%.

The sensor preferably includes an electrically isolated heating element in thermal contact with the oxide layer (referred to below as a heated sensor).

According to the invention in a second aspect, gas sensing apparatus including a resistive gas sensor, and resistance measuring means connected with the sensor, for measuring values taken by the electrical resistance of the sensor in response to the concentration of a target gas to which the sensor is exposed, is characterised in that the sensor is a sensor according to the said first aspect.

According to the invention in a third aspect, a method of measuring concentrations of ozone using a resistive gas sensor comprising a sensing element containing tungsten trioxide as gas-sensitive material, is characterised in that the sensor is a heated sensor, the method including exposing the sensor, at a working temperature in the range from ambient to 600° C., to concentrations of ozone in air in a range that includes at least from 0 to 1 parts per million inclusive, and measuring values taken by the resistance of the sensing element in response to the ozone concentration.

According to the invention in a fourth aspect, a method of making a sensor according to the invention in its first aspect is characterised by the steps of calcining $WO_3$ powder at a temperature of the order of 1000° C., subsequently applying the calcined material to a set of electrodes, and firing the material to a temperature substantially the same as the calcining temperature, whereby to retain the required high surface area and open porosity.

The invention thus provides a method of sensing ozone concentrations below 1 ppm in air, which comprises exposing to air an electrical resistance sensor, comprising a porous film having an open micro-structure and containing $WO_3$ as the sensing material, and measuring electrical resistance signals from the sensor so as to detect the presence and/or concentration of ozone in the air.

It also provides a gas sensor, which has $WO_3$ as its sensing material, with a sufficiently open porous microstructure and high surface area to produce a measurable signal representing a change in electrical resistance of the sensor in the presence of ozone at concentrations of less than 1 ppm of ozone in air. It will however be understood that use of the sensor and method of the invention is not confined to the case where the ozone concentration is 1 ppm or less: the invention is also effective at higher values.

The $WO_3$ is preferably not doped, so that for example platinum is absent from the gas-sensitive material.

It is by careful control of the development of the microstructure of the gas-sensitive, porous $WO_3$ body of the sensor that the latter can be made, in accordance with the invention, in such a way that it is able to detect ozone at the very low concentrations at which monitoring to prevent occupational exposure to hazardous levels of the gas is required.

The invention will now be discussed further, by way of example only and with reference to the accompanying drawings, in which:

FIG. 1 shows response characteristics of a sensor according to the invention to ozone concentrations of 0 to 0.3 ppm in air;

FIG. 2 is a similar diagram on a logarithmic scale;

FIG. 3 shows the cross-sensitivities of such a sensor as between ozone and three other gases, given by way of example;

FIG. 4 shows diagrammatically a simplified form of a typical apparatus for conditioning and calibrating an ozone sensor;

FIG. 5 shows diagrammatically a test chamber of the apparatus of FIG. 4, with electrical connections;

FIG. 6 shows responses of an unconditioned sensor to ozone;

FIG. 7 shows responses of a sensor conditioned by short-term repetitive exposure to ozone;

FIG. 8 shows signal variation when a sensor is powered-up in the presence of ozone;

FIG. 9 shows sensor response for different ozone concentrations in a pulsed power mode;

Figure 12:
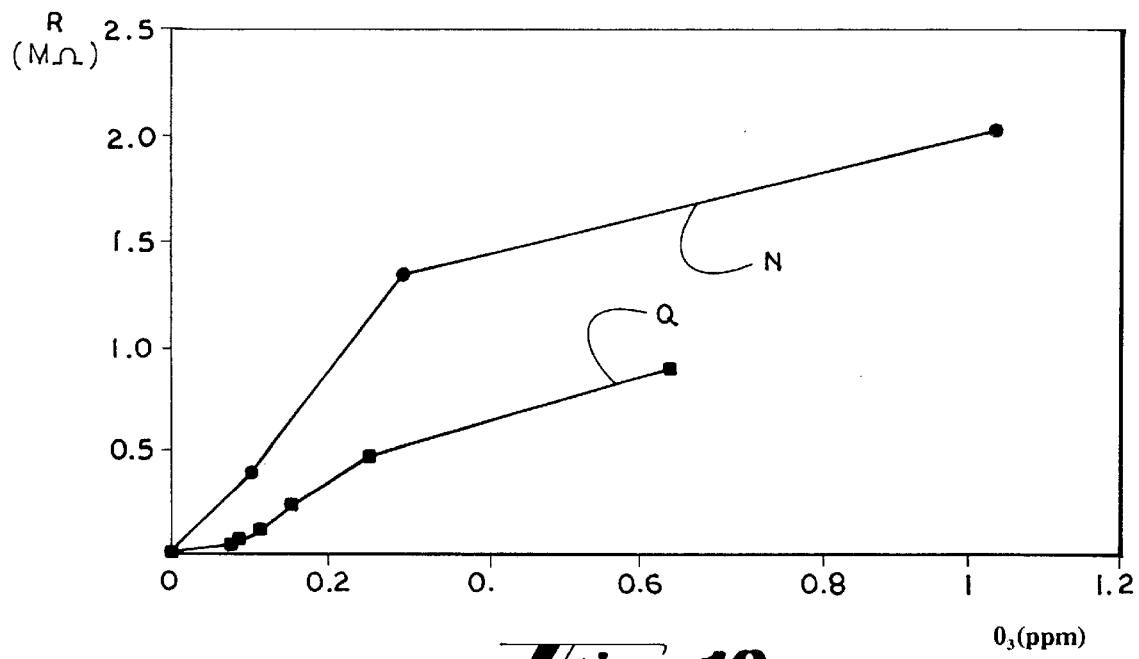
Figure 13:
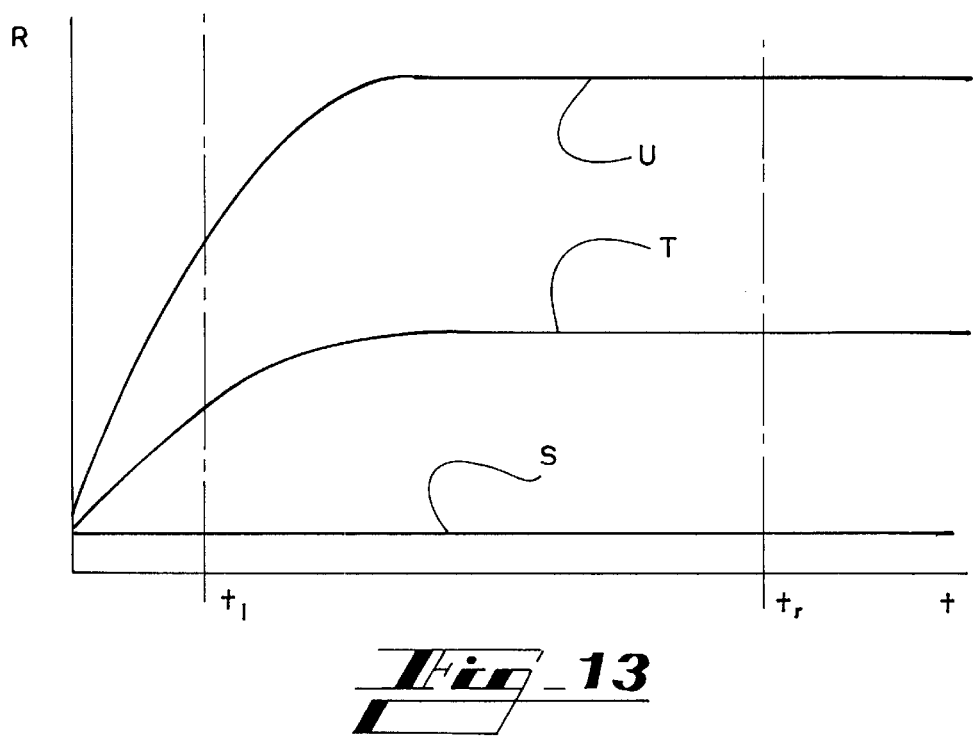

FIG. 10 compares responses of a sensor to ozone when operating under pulsed power and under continuous power;

FIG. 11 shows, for two sensors, responses to varying ozone concentration under pulsed and continuous power;

FIG. 12 compares the response of an ozone sensor with and without a cap;

FIG. 13 shows response curves for an ozone sensor at three different ozone concentrations;

FIG. 14 is a diagrammatic view, not to scale, showing one form of construction of an ozone sensor according to the invention, in cross section on the line XIV—XIV in FIG. 15;

FIG. 15 is an outside view of the same sensor, with the tungsten oxide layer omitted;

FIG. 16 shows a typical mounting for the sensor, in cross section taken on the line XVI—XVI in FIG. 17;

FIG. 17 is an outside view of the mounting shown in FIG. 16, with the cap removed; and FIG. 18 is a block diagram illustrating in simple form an ozone sensing apparatus incorporating a sensor according to the invention.

Air is continuously monitored, using gas monitoring equipment (not shown), which may be generally conventional in that it consists of one or more gas sensors and equipment of any suitable known kind for receiving, processing and making any suitable use of electrical resistance signals from the sensors. For example, the equipment, connected to at least one sensor according to the invention, can be arranged to give suitable warnings when the concentration level of ozone in the atmosphere rises above a predetermined safety level, which is generally less than 1 ppm.

The sensors in this case consist of interdigitated electrodes on which a thick film of gas sensitive material is screen printed. The mechanical construction of the sensor can be generally conventional; but an example of a suitable construction is described later herein.

The gas sensitive material is $WO_3$, which is of a typical purity exceeding 99%. Typical impurities are: $ZrO_2$ (30 ppm), sodium (20 ppm), and Mg, Cd, Mn, Fe, Cu, Ca (each less than 30 ppm).

By way of example, the sensor is made by calcining $WO_3$ as a loose powder at 1000° C. in air for 16 hours, after which it is cooled to room temperature and mixed with a suitable organic vehicle so as to produce an ink for screen printing. This ink is then printed over the electrodes, and fired to a top temperature that is the same as the calcination temperature. This results in a particularly large amount of surface area in the pores of the structure, and a particularly open porosity, being retained in the thick film.

In use, the sensor is heated to a temperature in the inclusive range from ambient to 600° C., and typically 400° C.±20° C., and is exposed continuously to the atmosphere in which any ozone is to be detected.

The emphatic resistance response of the sensor to the introduction of ozone into ambient air, at least at concentrations below 1 ppm, can be seen in the characteristics in FIGS. 1 and 2 for the range of 0–0.3 ppm (300 ppb). In FIG. 1, the lines A and B are taken at 80% and 45% relative humidity (RH), respectively. In FIG. 2, the lines A' and B' are the logarithmic equivalents of lines A and B respectively, the phantom line being a line of proportionality approximating to the lines A' and B'.

FIG. 3 shows the response of the resistance R of such a sensor to ozone in this concentration range, as compared with its response to $NO_2$, chlorine and $H_2S$ which are present at the same time. In FIG. 3, the line C represents the response to ozone, D represents the response to $NO_2$, and E the response to chlorine and $H_2S$. It will be realised from FIG. 3 that the response signal can readily be processed, in any suitable known way, so that weak signals such as those due to the three last mentioned gases are ignored by the processing equipment. In this connection, we have found with some surprise that these sensors, made in accordance with the invention, are selective not only in the way exemplified by FIG. 3, over $NO_2$, chlorine and $H_2S$, but also over other gases as well, for example (but without limitation), carbon monoxide, hydrocarbons, ammonia, hydrogen and ethanol.

More surprisingly, we have discovered that the curves relating sensor resistance to ozone concentration illustrated in FIGS. 1–3 will in practice tend to depend upon the prior history of the sensor, and also on all the materials in its immediate vicinity. Ozone is adsorbed on to, and can interact with, many surfaces, and also with other molecules which may be present, such as hydrocarbons and oxides of nitrogen. It may also be adsorbed on to nearby surfaces. One important species which can reduce the ozone concentration experienced by the sensor, either through its presence either in the gas phase or when adsorbed on surfaces near the sensor, is water vapour.

When the surfaces or atmosphere are hot, which they inevitably are if the sensor element or chip is operated continuously at its normal operating temperature such as 400° C., these problems of establishing a concentration of ozone in the vicinity of the sensor representative of the surrounding wider atmosphere are exacerbated. This is because ozone decomposes and reacts more rapidly at higher temperatures.

When calibrating ozone sensors it is important to remember that ozone is a strong oxidising agent. A steady state concentration in any environment is established only slowly, because the gas adsorbs on most containing surfaces and is itself reduced to varying degrees, depending on the nature of the surface, temperature, humidity and hydrocarbon contamination. In the real atmosphere remote from any surfaces, the ozone concentration will have reached a steady state: it is this concentration that the sensor should, as far as is at all possible, be adapted to measure.

Out of doors, the ozone concentration is determined by the intensity of sunlight and the concentration of hydrocarbons and oxides of nitrogen in the atmosphere. Indoors, the concentration is determined by the balance between the rate of production of the gas and by its rate of decomposition, and can vary widely depending on the location of the ozone sources in relation to the measurement point.

The kinetics of the sensor response are influenced by relative humidity: an artificial atmosphere of dry ozone gas induces a slower response and is misleading, since artificially maintained and managed laboratory conditions of this type do not reflect the real atmosphere.

It can be seen from the foregoing that the calibration procedure for the ozone sensor should involve a conditioning process which leads to its evaluation, or response characterisation, in order to stabilise the sensor under the conditions in which it is then to operate in service.

FIGS. 4 and 5 show a typical apparatus for use in this calibration process. The apparatus comprises an ozone generator 10, fed with pure dry air at 12. The air/ozone mixture leaving the generator is passed via a pipe 14 to a junction 16 between the pipe 14 and a further feed pipe 18. Pure dry air is passed through the pipe 18, via a flow controller 20 and a controllable humidifier system 22, to the junction 16, where it mixes with the air/ozone mixture.

The humidifier 22 is represented here, by way of example, in the form of a vessel 24 containing pure water, connected to the pipe 18 via a valve 26 and a valve 28 downstream of the valve 26. The valves 26 and 28 control communication between the pipe 18 and two branch tubes 30, 32 terminating in the vessel below and above the level of water in the latter, respectively. Thus the valves switch between wet and dry conditions. When they are open, the air reaching the junction 16 from pipe 18 is wet.

The humidifier can of course take any other convenient form.

A sensor test chamber 34 has an inlet 36 immediately downstream of the junction 16. The test chamber 34 has as small an internal surface area as is practical, and is preferably made from laboratory glass or anodised aluminium. After leaving the test chamber part of the gas stream is diverted through a UV ozone analyser 38, which continuously monitors the ozone concentration. If required, a signal from the analyser can be employed in a feedback network (not shown), having an appropriate time constant to maintain the ozone concentration in the test chamber 34 at a fixed level. Care needs to be taken to establish a stable and uniform ozone concentration in the test chamber, by allowing adequate purging of the equipment and by correlation of the output ozone level of the ozone generator 10 with that measured by the analyser 38.

Power is applied from a pulsed 5V power supply unit 40 to a sensor heating driver 42, connected via leads 44 to connections in the chamber 34, which are in turn connected to the heater of the sensor 46 in the chamber. The resistance signals from the sensor are taken to the appropriate measuring equipment via leads 48.

When power is applied to the driver 42, the sensor temperature stabilises at the operating temperature within 10 seconds. In air not containing ozone, the sensor resistance falls rapidly, goes through a minimum, then rises, and stabilises at the baseline resistance value in about one minute. In air containing ozone, the behaviour of the sensor depends to some extent upon its previous history of exposure to ozone. We believe that this is because the concentration of ozone in the immediate vicinity of the active sensor surface changes as ozone scavenges adventitious hydrocarbon contamination off the surrounding surfaces.

The pipework in the apparatus of FIGS. 4 and 5 is preferably made of polytetrafluorethylene (PTFE).

A suitable conditioning and response characterisation procedure for sensors involves:
- adjusting their operating temperature to the required level over a period of typically ten minutes in air of ambient humidity;
- allowing the sensors to cool for typically five minutes;
- introducing a stable concentration of ozone into the test volume of typically 300 ppb concentration in 50% nominal relative humidity;
- powering the sensors at the previously adjusted temperature for typically 30 minutes;
- allowing the sensors to cool for typically five minutes;
- powering the sensors for 95 seconds; and
- measuring their resistance at the end of this interval.

The desirability of conditioning is illustrated by reference to FIGS. 6 and 7. In FIG. 6, the resistance response R, over 15 hours at 400° C., of a sensor which has not been conditioned in moist air and moist ozone is shown, for ozone concentrations of 1 ppm (curve F) and 100 ppb (curve G), the ozone being introduced at the time O. In curve F, the resistance of the sensor rises rapidly to a high value, then slowly increases further up over a continued long period of exposure. In curve G, the sensor resistance rises through a maximum, decreases to a minimum, then rises slowly once more. The details of this time variation of the sensor resistance vary from one sensor to another, and change with changes in the relative humidity of the atmosphere. Ozone-containing air delivered from a typical generator can be extremely dry, since ozone also reacts with water vapour. Even at the elevated temperature of operation, the sensor surface retains traces of strongly-bound water, and some of the time-variation of resistance can be ascribed to the effects of the very dry atmosphere slowly further drying the sensor surface. Since the effects are particularly marked at low ozone concentration, it is also believed that these time-variations are partly due to changes in the actual concentration of ozone at the active sensor surface, caused by changes in the rate of decomposition of the gas on adjacent surfaces.

After short-term repetitive exposure to dry ozone, on the other hand, a reproducible characteristic can be obtained, as shown in FIG. 7. FIG. 7 is a plot of sensor response against time, showing a sequence in which the sensor was continuously exposed to dry air, with ozone added, in the concentrations indicated, for the periods marked "$O_3$". This Figure shows that, although during the first exposures, first to 1 ppm and then to 0.3 ppm ozone, the sensor did not fully stabilise in the time allowed, stabilisation did occur subsequently.

In use, there are two possible modes of sensor operation: continuously powered and pulse powered. We have found that the pulse powered mode of operation gives more consistent results at low ozone concentrations. We believe that this is because there is less uncertainty in this mode of operation about the actual ozone concentration in the immediate vicinity of the sensor: the sensor operates at an elevated temperature, and so warms up the surrounding surfaces. Ozone will be decomposed on these surfaces, so the actual concentration of gas in the vicinity of the sensor will depend critically upon the rate at which gas is flowing over the active surface.

However, in some applications operation under continuous power in dry ozone is suitable. Under continuous power, the sensor signal increases as the operating temperature is decreased. At an operating temperature of 200° C., the device is extremely sensitive, so much so that any minor change in ozone concentration at low concentrations will result in very large changes in sensor signal. At operating temperatures lower than 200° C., the response to the introduction of ozone into the air does however become slow.

In pulse powered operation, the sensor is initially at room temperature. Power is applied and the resistance measured after a short predetermined time delay from the start of each discrete pulse. We have used a delay of 75 seconds. Although the sensor signal does not stabilise in this time, we have found that this simple procedure is effective, because both the final sensor resistance and the initial rate of rise of resistance following the stabilisation of the temperature increase regularly with increasing ozone concentration. The procedure can readily be refined so that the rate of change of sensor resistance can be measured after a short time delay.

As a consequence of the reactivity of ozone to adventitious contamination on surfaces, depending on how long the sensor has been left unpowered, it may be necessary to apply two pulses and take the result of the second pulse. This is because, if a sensor has been left unpowered, there may be a delay before the signal is observed. This can be because there is some adventitious hydrocarbon contamination on the surface which scavenges the ozone, or because the sensor surface might be rather wet as a consequence of exposure to ambient atmospheres of high relative humidity with which ozone reacts. Second and subsequent pulses can, however, be expected to give generally consistent results. The "cleaning" caused by heating in ozone lasts for some time, so any subsequent heating pulse, applied within some hours of the first, can also be expected to give a consistent result.

FIG. 8 shows the signal variation when a sensor is powered up (i.e. when power is initially applied) in the presence of ozone. This measurement was made, in the way described later herein, with a relative humidity of 30% in the gas stream, and illustrates both continuous power and pulsed power operation. The heater driver was adjusted to give the required operating or working temperature (400° C.) in air at 30% RH (region H), and was then switched off. Ozone was introduced into the gas stream at a concentration of 100 ppb, and the concentration in the exit stream allowed to stabilise at 100 ppb (region I). Power was applied to the sensor again (region J), and maintained for 30 minutes. The sensor was again switched off, for 10 minutes (region K). The power was pulsed on again and the resistance measured after 75 seconds (region L). If the power is continued, then the sensor resistance will, in general, rise above its steady state value attained in region J.

FIG. 9 shows the variation with ozone concentration of the sensor resistance measured after 75 seconds, as described above, in the pulse powered mode of operation.

FIG. 10 shows, for each of the three concentrations of ozone indicated (100 ppb, 300 ppb and 1 ppm), the response curves M obtained in a continuous power mode, overlaid on the responses observed under the same conditions but in a pulsed power mode. In the latter case, pulses were applied at 5-minute intervals, power being switched on where indicated at 50 for each pulse, and off where indicated at 52. The sensor resistance measured after 75 seconds of each pulse is indicated at $R_{75}$ in each case, the data points shown having been taken at 6-second intervals during each pulse.

In FIG. 11, the resistance R of a first sensor to ozone at different concentrations is shown for the continuous power mode (line 1C) and for the pulsed power mode (line 1P). Similar responses 2C and 2P respectively are shown for a second sensor. The pulsed power resistance was measured after 75 seconds in each case, as before.

As an illustration of the effects of reactive surfaces in the vicinity of the sensor, FIG. 12 shows a response curve for a sensor tested under continuous power in a housing such as that described later herein with reference to FIGS. 16 and 17, having a removable cap 102. The sensor was tested with the cap on (line Q), and then with the cap removed (line N). The low concentration response of the sensor without the cap is enhanced.

The behaviour of the ozone sensor can be understood phenomenologically by the response curves illustrated schematically in FIG. 13, in which sensor resistance R is plotted against time t for three ozone concentrations, namely zero (response S), 100 ppb (response T), and 300 ppb (response U).

As has already been indicated herein, the rate of rise of resistance of the sensor depends on its intrinsic response (including its previous history), the means by which ozone reaches the sensors, the surrounding materials and gases and their temperatures. Similarly the "steady state" resistance response of a sensor to gas, which may not be entirely steady over extended periods of time, depends on these factors. Consistent measurements can be made satisfactorily, as FIGS. 7 and 10 illustrate, if the sensor is exposed to consistent conditions when measurements are taken. In this connection, for optimum performance, sensors should be either calibrated in situ, or deployed exactly as they have been calibrated, for example as described earlier herein.

FIGS. 14 and 15 show, somewhat diagrammatically, a typical form of construction for the ozone sensor. In this example the sensor, 68, comprises a metal oxide substrate 70, carrying a pair of interdigitated metallic electrodes 72 on one of its faces, 74. On its other face 76 the substrate carries a heating element 78 which is electrically insulated, there being an insulating layer 80 overlaid on the face 76.

A porous tungsten oxide layer 82 (omitted in FIG. 15), which is the active component of the sensor, is carried by the substrate 70. The layer 82 is made using the conventional thick-film processing method described earlier herein. It should be noted that sensors made using that method are found to have repeatable characteristics in terms of their ozone and temperature response.

The layer 82 is in electrical contact with the electrodes 72, and is bonded on the latter and on the face 74 by sintering, being in thermal contact with the heater element through the substrate 70. The thickness T of the layer 82 is greater than 50 $\mu$m and uniform across the layer within ±20%. It is repeatable between one sensor and another to better than ±20%.

The layer 82 is free from macroscopic flaws, such as cracks or bubbles, larger than 5 times the mean pore size of the tungsten oxide, the porosity of which is in the inclusive range 30–60%. It consists of particles of $WO_3$ having a purity of at least 99% and a particle size preferably smaller than 5 $\mu$m. No isolated particle has a dimension larger than 5% of the thickness T.

The substrate 70 in this example is of alumina, with a thickness in the inclusive range 0.2–3 mm. The electrodes 72 are of a metallic material, such as platinum or gold, appropriate for use with ozone and tungsten oxide. They are spaced apart by a distance d which is in the inclusive range 1–300 $\mu$m, the value of d being chosen so as to give a range of electrical resistance between the electrodes convenient for measurement in the application for which the sensor is intended to be used. The distance d is generally uniform within ±5%, and a typical value of d is 200 $\mu$m where the layer 82 is of $WO_3$ with gold electrodes.

It will of course be understood that the sensor may be of any other convenient form. The substrate may for example have a suitable metal oxide composition consisting of, or containing, at least one oxide other than alumina. The sensor need not be flat as shown, but may have another shape, such as that of a cylinder. The $WO_3$ sensing material may be incorporated in a suitable multi-state ceramic composite, in any known way but such that its response to ozone is substantially that of the $WO_3$ alone.

Each electrode 72, and each end of the heater element 78, is suitably connected electrically to an external terminal connection, in this example in the form of a tag or pad. In this example the pads 90 for the electrodes are on one side of the sensor 68, and the pads 92 for the heater are on the other, with one pad at each corner. These terminal connections may of course be located in any convenient position on the sensor, but the "four-cornered" arrangement shown here is especially suitable for enabling the sensor to be suspended freely in a housing, so that the gas under test can flow around the sensor. This assists dissipation of heat from the sensor when the heater element 78 is energised in use. In this connection it is desirable to keep the heated part of the sensor well spaced away from the inner surface of the housing.

An example of such a housing is shown at 94 in FIGS. 16 and 17. It comprises a cylindrical base 96 having a base portion 98 and a coaxial cylindrical wall 100 extending from the latter. A removable cap 102 fits around the wall 100, and has slots 104 for admitting the gas under test into the interior of the housing. The base portion 98 carries external pins 106 for soldering to a printed-circuit board, each pin 106 being connected within the base 96 to terminal posts 108 on top of the wall 100.

The housing 94 may be of any suitable material, but in this example it is of a material impervious to ozone, such as polyphenylene sulphide, gold-plated metal, or anodised aluminium.

The sensor 68 is suspended within the housing, in the cavity 110 within the wall 100, by four platinum wires 112. Each of these is attached to a respective post 108 at one end, and to a respective pad 90 or 92 at the other. The length of each wire 112 is such that the sensor is more than 3 mm away from any surface of the housing, and their diameter is typically 100 µm or less.

The wires 112 also provide part of the electrical connection between the electrodes and heating element of the sensor on the one hand, and parts of the ozone detecting apparatus which either supply power to the heater, or receive resistance signals from the sensor, on the other. In this connection, the electrical resistance of the wires 112 should be no greater than 5% of the resistance of the sensor heating element 78, and their length and diameter should generally be such that no more than 30% of the power dissipated in the element 78 is conducted down any one wire 112.

An ozone detecting apparatus is illustrated, very simply and generally, in FIG. 18. A power source 120 supplies power at suitable voltages to a heating control means 122 and to a resistance measuring circuit 124. The heater 78 of the sensor 68 is connected to the output side of the control means 122, while its electrodes 72 are connected to the input side of the circuit 124. The measuring circuit 124 processes the sensor output signals and produces output signals, representing sensor resistance, in any suitable form. These output signals may for example be taken to output means 126, such as a VDU, or means for giving a visual or audible indication of the presence of any ozone or of an excess amount of ozone.

The elements 120, 122, 124 and 126 may take any well-known form, depending on particular requirements, and need not be described further: however, it should be noted that the heating control means are preferably arranged to control the working temperature of the oxide layer 82 to within ±0.1° C., and to maintain the temperature across the layer 82 uniform within ±30° C.

It should also be noted that, when the sensor according to the invention is in use for detecting ozone, care must be taken not to induce polarisation within the sensor when measuring the sensor resistance. This can conveniently be achieved by using an impressed current of around 10 µA.

What is claimed as invention is:

1. An electrically resistive gas sensor comprising a sensing element containing tungsten trioxide as gas-sensitive material, wherein the sensing element is a porous oxide layer of a known mean pore size, open porosity and surface area, said porous oxide layer containing tungsten trioxide which is at least 99% pure, its porosity being in the inclusive range 30–60%, macroscopic flaws having a dimension larger than 5 times the mean pore size being absent, and said layer having a thickness of less than 50 micrometer and uniform to an accuracy better than ±20%.

2. A sensor according to claim 1, wherein tungsten trioxide in the said oxide layer has a maximum particle size smaller than 5 micrometer.

3. A sensor according to claim 1, wherein oxide particles having a dimension greater than 5% of the thickness of the said layer are absent from said layer.

4. A sensor according to claim 1, having a metal oxide substrate in electrical contact with the said oxide layer and a pair of interdigitated metallic electrodes carried by the said substrate and in electrical contact with the said oxide layer, the distance between the electrodes of said pair of electrodes being uniform to better than ±5% and in the inclusive range 1–300 micrometer.

5. A sensor according to claim 1, wherein the said oxide layer consists of a multi-phase ceramic composite having a response to the presence of ozone which is substantially that of tungsten trioxide alone.

6. A sensor according to claim 1, wherein the thickness of the said oxide layer is in the range 5–200 micrometer.

7. A sensor according to claim 6, characterised in that the said thickness is 40 micrometer.

8. Gas sensing apparatus including a resistive gas sensor according to claim 1 and resistance measuring means connected with the sensor, for measuring values taken by the electrical resistance of the said sensor in response to the concentration of a target gas to which the said sensor is exposed.

9. Apparatus according to claim 8, said sensor further having an electrically isolated heating element in thermal contact with said oxide layer, heating control means connected with said heating element, wherein the said heating control means is adapted to control the temperature of the said oxide layer to an accuracy better than ±0.1° C. and to maintain the temperature across the said layer uniform within ±30° C.

10. Apparatus according to claim 8 and further including a sensor housing containing said sensor and having electrical connection means for connecting said sensor with at least the resistance measuring means, wherein the said housing comprises a base carrying the said sensor, and a removable cap having means for admitting gas to the said sensor.

11. Apparatus according to claim 8 further including a sensor support means comprising a plurality of fine wires suspending the said sensor in free space, the said wires being electrically connected to the said sensor and to connection means for connecting the said sensor with at least the said resistance measuring means.

12. Apparatus according to claim 11 in which the sensor includes an electrically isolated heating element in thermal contact with the said oxide layer, wherein the said wires have an electrical resistance no greater than 5% of the resistance of the heating element, the length and diameter of the wires being such that no more than 30% of the power dissipated in the heating element can be conducted along the said wires.

13. A method of measuring concentrations of ozone using an electrically resistive gas sensor comprising a sensing element, wherein the said sensing element is a porous oxide layer, containing tungsten trioxide as gas-sensitive material, wherein said resistive gas sensor is made in accordance with claim 1, in which said sensor includes an electrically isolated heating element in thermal contact with said oxide layer, the method further including the steps of applying power to said heating element so as to heat said sensing element to a working temperature above ambient, and controlling the working temperature to an accuracy within ±0.1° C., and maintaining the temperature across the said sensing element uniform within ±30° C.

14. A method according to claim 13, wherein the working temperature is in the range 300°–520° C.

15. A method according to claim 13, wherein the power is applied in one or more discrete pulses, the resistance being measured after a predetermined time from the start of a pulse.

16. A method according to claim 13, further including the preliminary procedure of conditioning and calibrating the sensor by:
   (i) heating the sensor to a predetermined temperature corresponding to a required working temperature, over a first time period in air;
   (ii) allowing the sensor to cool;
   (iii) introducing ozone to the sensor in a stable known concentration;
   (iv) reheating the sensor to the same temperature as in step (i), for a second time period;
   (v) repeating step (ii); and
   (vi) reheating the sensor, and measuring its resistance after a predetermined time period.

17. A method according to claim 14, wherein the working temperature is 495° C.±10° C.

18. A method of making a sensor according to claim 1, including the steps of calcining $WO_3$, powder at a temperature of the order of 1000° C., subsequently applying the calcined material to a set of electrodes, and firing the material to a calcining temperature substantially the same as the calcining temperature, whereby to retain the required high surface area and open porosity.

* * * * *